United States Patent
Dries

(10) Patent No.: US 10,479,740 B2
(45) Date of Patent: *Nov. 19, 2019

(54) PROCESS TO PREPARE PROPYLENE

(71) Applicant: GASOLFIN B.V., Amersfoort (NL)

(72) Inventor: Hubertus Wilhelmus Albertus Dries, De Steeg (NL)

(73) Assignee: GASOLFIN B.V., Amersfoort (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/737,830

(22) PCT Filed: Jun. 23, 2016

(86) PCT No.: PCT/NL2016/050444
§ 371 (c)(1),
(2) Date: Dec. 19, 2017

(87) PCT Pub. No.: WO2016/209074
PCT Pub. Date: Dec. 29, 2016

(65) Prior Publication Data
US 2019/0002369 A1    Jan. 3, 2019

(30) Foreign Application Priority Data

Jun. 23, 2015 (NL) .................................... 2015016

(51) Int. Cl.
*C07C 4/06* (2006.01)
*C10G 11/05* (2006.01)
(Continued)

(52) U.S. Cl.
CPC .................. *C07C 4/06* (2013.01); *B01J 21/04* (2013.01); *B01J 21/08* (2013.01); *B01J 21/12* (2013.01);
(Continued)

(58) Field of Classification Search
CPC .......... C07C 4/06; C07C 5/48; C07C 5/3337; C07C 2529/40; C07C 2529/85;
(Continued)

(56) References Cited

U.S. PATENT DOCUMENTS 2,322,366 A    6/1943    Kassel
2,331,427 A *  10/1943   Schulze ................. B01J 8/0285
                                                   208/135

(Continued)

FOREIGN PATENT DOCUMENTS

EP    2644584 A1    10/2013
WO    03/082462 A2  10/2003

OTHER PUBLICATIONS

Krylova (Products of the Fisher-Tropsch Synthesis, Solid Fuel Chemistry, 2014, vol. 48, No. 1, pp. 22-35) (Year: 2014).*

*Primary Examiner* — Philip Y Louie
*Assistant Examiner* — Jason Y Chong
(74) *Attorney, Agent, or Firm* — Nixon Peabody LLP; Ronald I. Eisenstein; Nicole D. Kling

(57) ABSTRACT

The invention is directed to a process to prepare propylene from a mixture of hydrocarbons by performing the following steps. (a) extracting aromatics from the mixture of hydrocarbons thereby obtaining a mixture of hydrocarbons poor in aromatics, (b) contacting the mixture obtained in step (a) with a heterogeneous cracking catalyst as present in a fixed bed thereby obtaining a cracked effluent, (c) separating propylene from the cracked effluent thereby also obtaining a higher boiling fraction, (d) recycling part of the higher boiling fraction to step (b) and at least 5 wt % of the higher boiling fraction to step (a).

18 Claims, 2 Drawing Sheets

Figure 1:
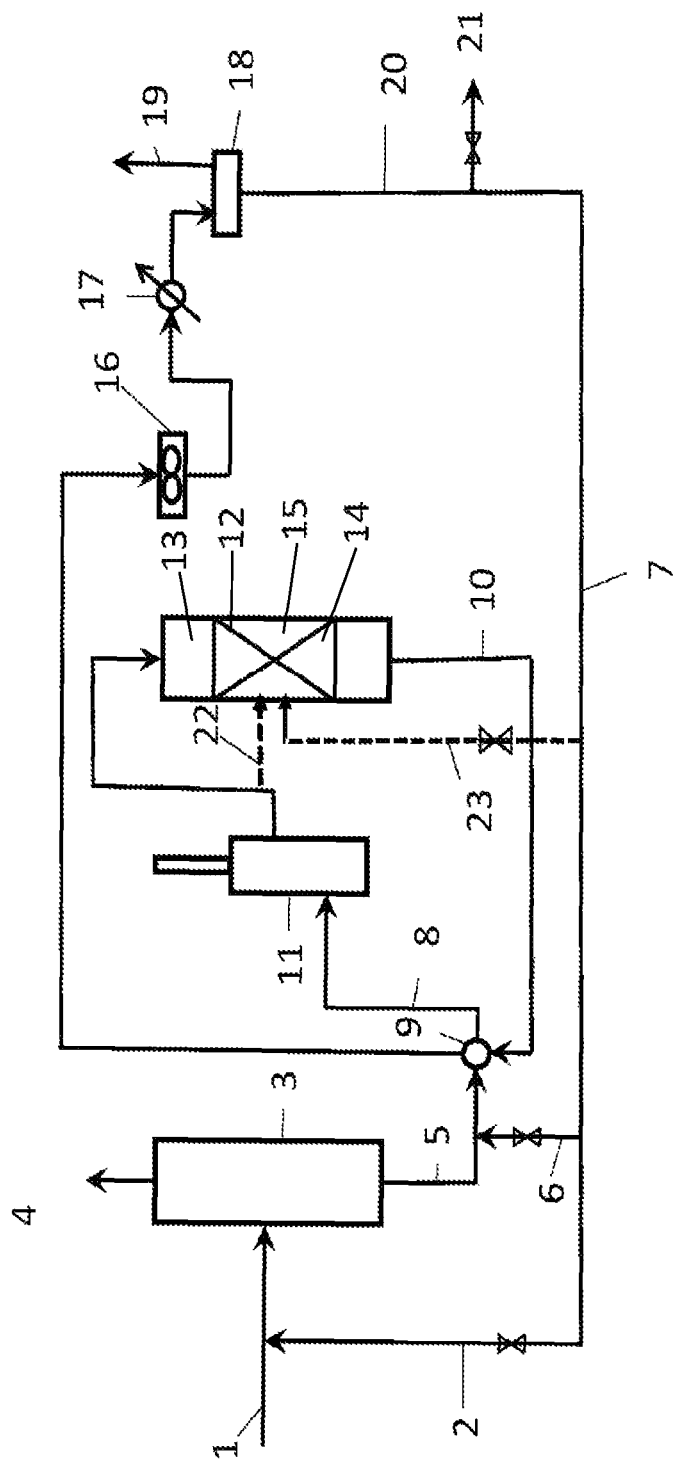

(51) Int. Cl.
| | |
|---|---|
| C10G 35/04 | (2006.01) |
| C10G 7/08 | (2006.01) |
| C10G 11/10 | (2006.01) |
| C10G 11/18 | (2006.01) |
| B01J 21/04 | (2006.01) |
| B01J 23/62 | (2006.01) |
| B01J 29/40 | (2006.01) |
| B01J 29/85 | (2006.01) |
| B01J 35/00 | (2006.01) |
| C07C 5/333 | (2006.01) |
| C07C 5/48 | (2006.01) |
| B01J 21/08 | (2006.01) |
| B01J 21/12 | (2006.01) |
| B01J 23/26 | (2006.01) |
| B01J 23/42 | (2006.01) |
| B01J 29/18 | (2006.01) |
| B01J 29/70 | (2006.01) |
| C10G 35/06 | (2006.01) |
| C10G 35/095 | (2006.01) |
| C10G 35/14 | (2006.01) |
| B01J 37/28 | (2006.01) |

(52) U.S. Cl.
CPC .............. *B01J 23/26* (2013.01); *B01J 23/42* (2013.01); *B01J 23/626* (2013.01); *B01J 29/18* (2013.01); *B01J 29/40* (2013.01); *B01J 29/7007* (2013.01); *B01J 29/7015* (2013.01); *B01J 29/85* (2013.01); *B01J 35/0006* (2013.01); *B01J 37/28* (2013.01); *C07C 5/3337* (2013.01); *C07C 5/48* (2013.01); *C10G 7/08* (2013.01); *C10G 11/05* (2013.01); *C10G 11/10* (2013.01); *C10G 11/18* (2013.01); *C10G 35/04* (2013.01); *C10G 35/065* (2013.01); *C10G 35/095* (2013.01); *C10G 35/14* (2013.01); C07C 2521/04 (2013.01); C07C 2523/42 (2013.01); C07C 2523/62 (2013.01); C07C 2529/40 (2013.01); C07C 2529/85 (2013.01); C10G 2300/1088 (2013.01); C10G 2300/1096 (2013.01); C10G 2300/4081 (2013.01); C10G 2400/20 (2013.01); Y02P 20/52 (2015.11); Y02P 20/582 (2015.11)

(58) Field of Classification Search
CPC .. C07C 2521/04; C07C 2523/62; B01J 29/40; B01J 29/85; B01J 21/04; B01J 23/626; B01J 35/0006
See application file for complete search history.

(56) References Cited

U.S. PATENT DOCUMENTS

| | | | |
|---|---|---|---|
| 3,714,022 A * | 1/1973 | Stine | C10G 59/02 208/62 |
| 4,835,127 A | 5/1989 | Eastman et al. | |
| 2003/0181325 A1* | 9/2003 | Ou | B01J 23/002 502/302 |
| 2005/0075526 A1* | 4/2005 | Abrevaya | C07C 4/06 585/651 |
| 2010/0331590 A1 | 12/2010 | Majumder et al. | |

* cited by examiner

PROCESS TO PREPARE PROPYLENE

CROSS REFERENCE TO RELATED APPLICATIONS

This application is a 371 National Phase Entry of International Patent Application No. PCT/NL2016/050444 filed on Jun. 23, 2016 which claims benefit under 35 U.S.C. § 119(b) of NL Provisional Patent Application 2015016 filed on Jun. 23, 2015, the contents of which are incorporated herein by reference in their entirety.

FIELD OF INVENTION

The invention is directed to a process to prepare propylene from a hydrocarbon feedstock comprising olefin hydrocarbon compounds.

BACKGROUND OF INVENTION

Propylene is for more than 50% produced by steam cracking processes. Typical feedstock is straight run naphtha as obtained when refining a crude petroleum source which typically comprises of unsaturated compounds, like paraffinic and naphthenic compounds, and aromatic compounds. Steam cracking processes are very complex and for this reason alternative processes starting from naphtha feedstock have been described in US2010/0274063 and US2010/0331590. These processes involve a dehydrogenation step to increase the olefin compound contents followed by a olefin cracking step wherein propylene is formed.

Propylene is also prepared in a refinery environment as a by-products of the Fluid catalytic cracking (FCC) process. Since the late nineties, some FCC units have been operating at higher severity to achieve a propylene yield of 10-12 wt percent of the fresh FCC feed. To further increase the propylene yield, different processes have been developed around the FCC configuration in a refinery and it has been reported that propylene yields up to 20 wt % of fresh FCC feed have been achieved.

One way to increase the propylene yield is to add a medium pore zeolite to the FCC catalyst as for example described in DE4114874. Various variants have been developed wherein the medium pore catalyst and the FCC catalyst contact the hydrocarbon fractions in riser reactors. A development is a FCC process employing two risers as for example described in US2013158326. A disadvantage of these processes is that the medium pore zeolite catalyst will be subjected to a regeneration step together with the FCC catalyst which causes the medium pore zeolite catalyst to degenerate. A disadvantage of the dual risers is the complexity of the process and the inflexibility to control the yield of propylene in response to changing economics. This may be the reason that up to this moment very few dual riser FCC units have been build.

US2012/0071701 describes a process wherein a fraction comprising olefins and paraffins in the C4-C12 range as obtained in a FCC process is first contacted with a olefin conversion reactor. From the effluent of the olefin conversion reactor light olefins, like propylene, are isolated. The remaining fraction is sent to a dehydrogenation reactor. The effluent of the dehydrogenation reactor is recycled to the olefin conversion reactor. According to the description the olefin conversion reactor and the dehydrogenation reactor may be a fixed bed reactors, fluidized bed reactors or a continuous catalyst regeneration (CCR) system.

A disadvantage of the process of US2012/0071701 is the high coke formation in the dehydrogenation cracking reactor. This coke formation forces one to perform the dehydrogenation in a fluidised bed reactor applying a separate regeneration reactor resulting in a complex process.

WO03/082462 describes a process to prepare light olefins by contacting a feedstock with a catalyst having a dehydrogenation function, as provided by a V/Mg metal oxide component, and a cracking function, as provided by a SAPO-34 zeolite. The feed was contacted with this catalyst in a fixed bed downflow reactor. Although the use of a fixed bed is favourable the coke make of such a process is relatively high. This will result in that the catalyst will have to be regularly decoked. Furthermore when starting from mixtures of hydrocarbons also containing aromatics more coke forming is to be expected.

The aim of the present invention is to provide a simpler process for the preparation of propylene starting from a mixture of hydrocarbons comprising aromatic hydrocarbon compounds as may be obtained from a FCC process.

SUMMARY OF THE INVENTION

This aim is achieved by the following process.
Process to prepare propylene from a mixture of hydrocarbons by performing the following steps:
  (a) extracting aromatics from the mixture of hydrocarbons thereby obtaining a mixture of hydrocarbons poor in aromatics,
  (b) contacting the mixture obtained in step (a) with a heterogeneous cracking catalyst as present in a fixed bed thereby obtaining a cracked effluent,
  (c) separating propylene from the cracked effluent thereby also obtaining a higher boiling fraction,
  (d) recycling part of the higher boiling fraction to step (b) and at least 5 wt % of the higher boiling fraction to step (a).

The applicant found that when aromatics are partly separated from the hydrocarbon mixture before performing step (b) a more efficient process is obtained. It was also found that when at least 5 wt % of the higher boiling fraction obtained in step (c) is recycled to step (d) the volume of the flow to step (b) in a continuous process is significantly reduced for the same propylene production. A further advantage is that the process is performed in packed beds. Even though some regeneration will have to be performed the use of such packed beds, also referred to as fixed beds, greatly simplifies the process when compared to a fluidised bed reactor combined with a fluidised bed regenerator. This process provides for example a simple method to upgrade excess gasoline as produced within a crude oil refinery into much more desired propylene. Especially older refineries being designed for maximum gasoline yield and now faced with a declining gasoline demand could benefit from this invention. Further advantages will be discussed when describing the preferred embodiments.

SHORT DESCRIPTION OF THE FIGURE

Figure 2:
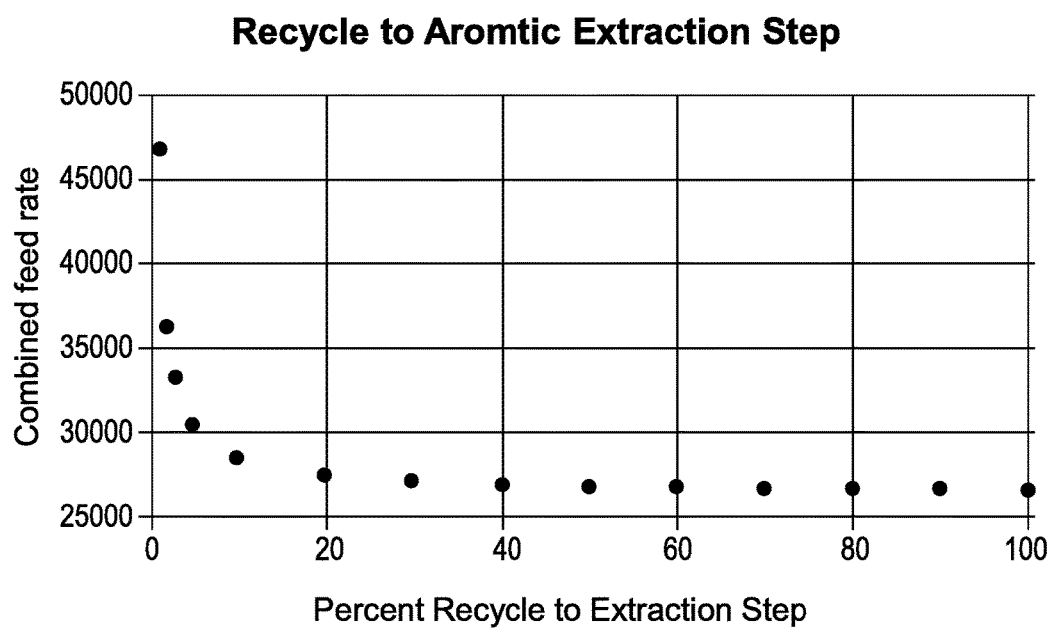

FIG. 1 describes a process flow scheme of a process to prepare propylene according to the invention.
FIG. 2 shows the influence of the recycle ratio in a process of FIG. 1.

DETAILED DESCRIPTION OF THE INVENTION

The mixture of hydrocarbons used in step (a) may be any mixture of hydrocarbons comprising paraffins, olefins, naphthenic and aromatic compounds. Suitably the feedstock is a mixture of these hydrocarbons boiling for more than 90 wt % between 35 and 250° C. The content of olefins having 4 or more carbon atoms in the feedstock is suitably between 1 and 100 wt %, preferably between 1 and 70 wt % and even more preferably between 1 and 50 wt % and most preferred between 1 and 20 wt %. Feedstock having a high olefin content, suitably higher than 5 wt %, are especially suitable to be converted by the process according to this invention to propylene. The feedstock may for example be any fraction as obtainable in a crude oil refinery having the above properties. Suitable feedstock may comprise a light straight run naphtha. Light Straight Run naphtha is a preferred feedstock because it is an extremely poor component to be directly used as part of a gasoline product. The Light Straight Run naphtha typically requires severe processing in a Catalytic Reforming Unit which is not advantageous because this will limit the cycle length of said Catalytic Reformer. Other refinery fractions, boiling in the above referred to range, suited to be used a feedstock or part of the feedstock are fractions as isolated from the effluent of a hydrogen depletion process, such as delayed cocker process and the fluid catalytic cracking process. A preferred feedstock are the fractions rich in hydrogen as isolated from the effluent of hydrotreating or hydrocracking processes. Another suitable fraction may be isolated from the effluent of a Catalytic Polymerisation Process. Other possible feedstock may comprise natural gas liquids, any other fraction boiling as described above and isolated from a refinery or chemical process. Even fractions as obtained from sources such as Fischer Tropsch synthesis, lube oil extracts, waxes or other hydrocarbon feeds boiling in the above referred to range may be contemplated.

Suitable refinery fractions are those isolated from the effluent of a fluid catalytic cracking (FCC) process are used as the feedstock or as part of the feedstock. Such a FCC unit may be operated with propylene enhancing additional catalysts, like the medium pore zeolite catalysts. The applicant has found that by using the process of this invention such use may be omitted and still prepare propylene in a high yield as calculated on fresh FCC feedstock. This is advantageous because less or no medium pore size zeolite is required to be supplied to the FCC process as replacement for degraded catalyst. The feedstock may be comprised of mixtures of this fraction and other fractions as described above. The feedstock will for its majority be comprised of the above hydrocarbons. Small amounts of for example water, sulphur compounds, nitrogen compounds may be present. The content of hydrocarbons in the feedstock will be above 95 wt %, suitably above 98 wt %.

The above mixture of hydrocarbons may be blended with pentane and iso-pentane as isolated from gasoline fractions in a refinery environment. It has been found to be desired to separate pentane and iso-pentane from these gasoline fractions in order to obtain a gasoline blending stock which is suited to meet the Reid vapor pressure (RVP) specification of motor fuels. By using these compounds as part of the olefinic feedstock a more desirable product like propylene is obtained.

Step (a) is important in the process according to the invention. Aromatics as present in the feed and present in the recycle stream are substantially inert in step (b). Aromatics have the effect of diluting reactants and increasing recycle stream rates. By extracting the aromatics from the fresh mixture of hydrocarbons fed to the process and also from part of the recycle stream a build-up of nonreactive aromatics in the recycle stream is avoided. Applicants have also investigated what would be the build up of aromatics when the aromatic extraction would be performed after performing step (c). For the investigated case the feed to the reactor containing the cracking catalyst in step (b) would be in tons/hour:

| Extraction according to invention | 26782 |
| No Extraction | 72214 |
| Post Extraction | 44187 |

The results above clearly show that by positioning the aromatic extraction step according to the invention a recycle stream is obtained which is 63% lower than operating the system without aromatic extraction. This is also results in that less feed to step (b) needs to be heated up which results in a more energy efficient process.

In step (d) part of the higher boiling fraction is recycled to step (b) and at least 5 wt % of the higher boiling fraction is recycled to step (a). Preferably between 5 and 80 wt % and more prefererably between 10 and 30 wt % of the higher boiling compounds are recycled to step (a) to be subjected to the aromatic extraction to avoid a build-up of aromatic compounds in the recycle.

In step (a) compounds such as benzene, toluene, xylene and para-xylene are separated from the mixture of hydrocarbons and recycle. Suitably more than 90 wt % of the combined benzene, toluene and xylene are extracted from the total feed to step (a) in step (a). Such an aromatics extraction step is well known and examples of suitable extraction solvents are diethylene glycol, tetraethylene glycol, diethylene glycol, dimethyl sulfoxide, sulfolane, N-formyl morpholine, N-methyl pyrrolidone, a glycol-glycol ether mixture and tertrahydrothiophene 1-1 dioxide. Because olefins may be present in the mixture of hydrocarbons as fed to step (a) an aromatic extraction process is preferred which is selective for aromatics in the presence of olefins. A suitable extraction process is an extractive distillation using one of the aforementioned solvents and suitably sulfolane, N-formyl morpholine or N-methyl pyrrolidone, optionally in combination with a suitable co-solvent. A suitable commercially available process is the so-called GT-BTX PluS type as developed and offered by GTC Technology, Houston Tex.

The heterogeneous cracking catalyst may suitably comprise an acidic material. Suitable acidic materials are those which can crack the gasoline range olefins to propylene. Such an acidic material may be a molecular sieve or a material having strong acid sites. A first type of heterogeneous cracking catalyst does not comprise a molecular sieve and does comprise a material having strong acid sites as the acidic material. A suitable acidic material is an amorphous or semi-crystalline material chosen from the group of heteropoly acids, alumina, boehmite alumina, gamma alumina, theta alumina, silica alumina, silica-titania, silica-tungsten, silica phosphorous, silica-alumina-phosphorous.

The acidic material may also be a molecular sieve. An advantage of a molecular sieve is the high acid site density per reactor volume. However, various molecular sieves increase hydrogen transfer and limit the propylene yield in this process. Thus depending on for example the type of feedstock and the choice of the dehydrogenation catalyst a choice regarding the most suited acidic material shall have to be made.

If a molecular sieve is used it is preferred that an optional carrier as part of the catalyst particles may have no strong acid sites, some strong acid sites or only strong acids sites.

The choice of suitable optional carrier will depend on the composition of the feedstock. Preferably the carrier does not have strong acid sites. The molecular sieve may have 8-membered oxygen ring channels such as Chabazite, also referred to as CHA structure type according to the Atlas of zeolite structure types, 4$^{th}$ rev. ed/W. M. Meier, D. H. Olson and Ch. Baerlocher. A typical example of such a molecular sieve is SAPO-34. The molecular sieve is suitably an intermediate pore-size zeolite. The term "intermediate pore-size zeolite" is meant to indicate any zeolite of which the pore size is intermediate between the pore size of a small pore-size zeolite such as typically A-type zeolite, and the pore size of a large pore-size zeolite such as typically mordenite, or X-type or Y-type zeolite". The intermediate pore size zeolite has a 10 or 12-membered oxygen ring in the crystal structure thereof. The zeolite suitably has a silica to alumina ratio between 10-300 and more preferred between 10-50. Examples of the intermediate pore-size zeolite are ZSM-5, ZSM-8, ZSM-11, ZSM-12, ZSM-21, ZSM-23, ZSM-35, ZSM-38. Preferably the molecular sieve is chosen from the structure types having a 10-ring channels according to structure types MFI, MEL, IMF, TUN and EUO. MFI is also known as ZSM-5, MEL is known as ZSM-11, IMF is known as IM-5 and TUN is known as TNU-9. Of this list MFI is most preferred in view of its availability combined with its performance.

The above molecular sieves may be present as such to provide the cracking catalyst. Suitably the molecular sieve is comprised in a carrier, wherein the weight content of the molecular sieve in the heterogeneous catalyst is between 5 and 70 wt %. The carrier may be silica, silica-alumina or alumina and may be suitably treated with phosphorous.

The invention is also directed to a process wherein next to propylene also butylene is isolated from the reaction products. In such a process it might be advantageous to obtain a relatively higher yield of butylene as compared to propylene. To achieve this the heterogeneous cracking catalyst suitably comprises a 12 member oxygen ring zeolites as the acidic material, preferably zeolite beta (BEA) and mordenite (MOR) are preferred. The acidic material may also be an amorphous or semi-crystalline acidic material such as alumina, boehmite alumina, silica-alumina, silica phosphate alumina, silica doped with phosphorous and silica doped with tungsten.

The cracking catalyst may be present in the fixed bed as discrete particles preferably having a volume mean diameter of between typically 1 mm to 3 cm.

Preferably the process is performed by contacting the mixture as obtained in step (b) in with a heterogeneous dehydrogenation catalyst in a step (b1) as present in a fixed bed. The effluent of step (b1) is the cracked effluent from which propylene is separated in step (c).

More preferably step (b) is performed by contacting the mixture obtained in step (a) with a mixture of a heterogeneous cracking catalyst and a heterogeneous dehydrogenation catalyst as present in one or more packed beds thereby obtaining propylene and other reaction products. The cracking catalyst and the dehydrogenation catalyst may for example be comprised in one particle as for example described in WO03/082462 and have a volume mean diameter of between 1 mm and 3 cm. Suitably the cracking catalyst and the dehydrogenation catalyst are present in one or more packed beds in an in-series configuration and wherein the hydrocarbon feedstock, formed propylene and other reaction products will flow from an up-flow region to a down-flow region following a flow path and wherein in the direction of the flow path the concentration of the dehydrogenation catalyst in the bed increases compared to the cracking catalyst. When the mixture obtained in step (a) is contacted as described less coking is found to occur as compared to when the process is performed by contacting with a homogenously mixed dehydrogenation and cracking catalyst or when the cracking catalyst and dehydrogenation catalyst are present in separate beds or reactors.

The cracking catalyst and the dehydrogenation catalyst are present in one or more packed beds in an in-series configuration. In this packed bed or beds the hydrocarbon feedstock, formed propylene and other reaction products will flow from an up-flow region to a down-flow region following a flow path. In other words the packed bed or packed beds in series will comprise such a flow path. Preferably the flow path runs from the first catalyst packed bed, the most up-flow catalyst bed, up to the last catalyst packed bed, the most down flow catalyst bed. The flow path may also consist of more than 80% or even more preferably more than 90% of such a maximum flow path length.

Preferably these compounds flow in a plug flow or semi-plug flow fashion through the packed bed or beds. Although some back mixing will occur the configuration of the packed beds is preferably so chosen that such back-mixing is avoided as much as possible. In one embodiment of the present invention the dehydrogenation catalyst and the cracking catalyst are present in the same ratio throughout the entire bed or beds or said otherwise along the entire flow path. This ratio may vary along the flow path.

The applicant found it to be advantageous when in the direction of the flow path the concentration of the dehydrogenation catalyst in the bed increases compared to the cracking catalyst. Such an embodiment is preferred when the feedstock comprises relatively more olefins than paraffins, preferably wherein the weight ratio olefins to paraffins is greater than 0.75:1. In such an embodiment relatively more cracking catalyst will be present in the up-flow region and relatively more dehydrogenation catalyst will be present in the down-flow region. It is believed that the lower coke make in such a packed bed or beds is lower because the local concentration of higher olefins, i.e. olefins having more than 6 carbon atoms, can be kept low. It is believed that high concentrations of these higher olefins cause coke make. By having relatively more of the cracking catalyst at the up-flow region of the flow path the higher olefins as present in the feedstock are immediately converted to lower olefins like propylene. When the ratio of dehydrogenation catalyst increases relatively to the cracking catalyst more higher paraffins will be dehydrogenated to higher olefins. The thus formed higher olefins are in turn converted to the lower olefins by the cracking catalyst which is admixed with the dehydrogenation catalyst. This will substantially reduce the coking tendency in the packed bed or beds and will allow the dehydrogenation reaction to go to near completion.

Preferably the cracking catalyst is present along the entire length of the flow path while the content of the dehydrogenation catalyst relative to the total content of heterogeneous catalyst particles as present in the packed bed or beds increases along the flow path length in the direction of the flow. The content of dehydrogenation catalyst may be zero at the start of the flow path and for example gradually or step-wise increase along the flow path length. The cracking catalyst and dehydrogenation catalyst are suitably separate particles each having a chosen composition and size. This simplifies the catalyst loading of the packed bed or beds. But the cracking catalyst and/or dehydrogenation catalyst may also have a variable composition along the length of the flow path. The cracking catalyst and dehydrogenation catalyst may even be comprised in one particle which composition varies along the length of the flow path such to achieve the above described desired ratio between the cracking catalyst or better said cracking catalyst functionality and the dehydrogenation catalyst or better said the dehydrogenation functionality.

If the cracking catalyst and dehydrogenation catalyst are separate particles each having a chosen composition and size the content of the dehydrogenation catalyst particles may vary along the path way as described below. The content in volume percent of the dehydrogenation catalyst particles relative to the total volume of catalyst particles suitably varies from between 0 and 100% at the start of the flow path more preferred between 1 and 100, more preferred between 5 and 100, more preferred between 20 and 100, to between 0 and 100% at the end of the flow path, more preferred between 5 and 95%, more preferred between 10 and 90, more preferred between 20 and 80%. More preferably the content in volume percent of the dehydrogenation catalyst particles relative to the total volume of catalyst particles varies from between 0 and 50% at the start of the flow path to between 20 and 80% at the end of the flow path. More preferably in process (ii) the content in volume percent of the cracking catalyst particles relative to the total volume of catalyst particles varies from between 5 and 50% at the start of the flow path to between 20 and 100% at the end of the flow path. The start of the flow path is defined as the first 20% of the length of the flow path. The end of the flow path is defined as the last 20% of the length of the flow path. The most preferred contents of dehydrogenation catalyst will depend on the chosen cracking catalyst and dehydrogenation catalyst and their catalytic activity at the conditions at which the hydrocarbon feedstock is contacted with the catalysts. Such optimal conditions may be found by simple trial and error by the skilled person.

If the separate or combined cracking catalyst and/or dehydrogenation catalyst particles have a varying composition and/or size along the length of the flow path the above optimal contents of the dehydrogenation catalyst will obviously be different. Next to the heterogeneous cracking and heterogeneous dehydrogenation catalyst other catalytically or non-catalytically active particles may be present in the one or more packed beds.

The heterogeneous cracking catalyst and the dehydrogenation catalyst may also be present as a structured packing. Both the catalyst types may be incorporated in one structured packing. If a gradient is desired as described above different blocks of structured packing may be used wherein the blocks have a varying ratio of the two catalyst types. By placing the blocks in a certain order the desired gradient may be obtained. Alternatively blocks may be used wherein one type of block comprises the cracking catalyst and another type of block comprises the dehydrogenation catalyst. By placing the blocks in a certain order and alternating the types a homogeneous mixture of both catalyst types according the invention is obtained. In such an embodiment the total number of blocks or zones along the flow path is preferably above 1, preferably above 5 and more preferably above 10. If one desired to obtain the above described gradient using uniform blocks of structured packing one may vary the flow path length of the alternating blocks of cracking catalyst and dehydrogenation catalyst. For example the total flow path length of the cracking catalyst structured packing may be longer in the first half of the flow path length and shorter in the second half of the flow path length relative to the flow path length through the dehydrogenation structured packing.

The dehydrogenation catalyst suitably comprises a transition metal or a noble metal, one or more additive components and a carrier. The transition and noble metals are defined as any element in the d-block of the periodic table, which includes groups 3 to 12 on the periodic table. Examples of suitable metals exhibiting dehydrogenation properties are especially Cr and Pt, though other metals such as Mn, Zn, Co, Cu, Ni, or mixtures of these can be used as well. It is known in the art to increase the stability of Pt with Sn to lower the deactivation by coke, and alkaline metals on support can improve the selectivity by strong metal support interaction. Suitable additive components are Sn, Ga, alkaline metal, alkaline earth metal or combinations. Examples of suitable carrier materials are alumina, silica-alumina, silica, Kaolin, anionic clay, spinel, diatomite.

A suitable dehydrogenation catalyst may be a zirconia-based catalyst comprising zirconia in an amount of at least 40 wt %, suitably between 50 and 90 wt %. The catalyst may also comprise other metal oxides as the additive component, for example oxides of one or more metals selected from the group consisting of scandium, yttrium, lanthanum, cerium, actinium, calcium and/or magnesium. If used, the metal oxide(s) other than zirconia is/are generally present in an amount of at most 10 percent by weight of the dehydrogenation catalyst. The catalyst may further comprise suitable carriers as described above incorporated into the catalyst in a total amount of generally at most 50 percent by weight of the dehydrogenation catalyst.

The dehydrogenation catalyst may also be a so-called oxydehydrogenation catalysts as described in WO03/082462 or U.S. Pat. No. 5,530,171 wherein next to the above transition metal the dehydrogenation catalyst comprises a solid oxygen source comprising a reducible metal oxide, such as for example a reducible metal oxide of at least a transition metal selected, suitably Bi, In, Sb, Zn, TI, Pd and Te. Possible solid oxygen carriers are $CeO_2$, doped cerium oxides and preferably $Bi_2O_3$. The solid oxygen source may also be part of a further separate catalyst particle as present in the packed bed or beds. The presence of a oxydehydrogenation catalyst is advantageous because it helps to drive the dehydrogenation reaction to completion and prevents the reverse reaction, the hydrogenation of olefins by the presence of hydrogen in the system.

The dehydrogenation catalyst may be present in the fixed bed as discrete particles preferably having a volume mean diameter of between typically 1 mm to 3 cm.

The overall ratio between the cracking catalyst and the dehydrogenation catalyst will depend on their relative activities. The relative rate of cracking over the cracking catalyst should preferably outpace the olefin generation over the dehydrogenation catalyst to limit the coke generation. As large olefins tend to make coke, it is preferred that the removal rate of large olefins exceeds the generation rate of these at every stage in the bed. As cracking rates and dehydrogenation rates depend on the local composition of the reaction mixture in the packed bed, their concentration (partial pressure), hydrogen partial pressure and temperature, these numbers can be obtained empirically or using kinetics obtained over the respective cracking catalyst and dehydrogenation catalyst. For example olefins, especially C7-C12 olefins, are found to rapidly crack to for example propylene when contacted with a ZSM-5 based cracking catalyst. Even up to C16 olefins, and especially normal-olefins, are found to easily crack. Also paraffinic waxes can be a prime feedstock to crack over ZSM-5. Though smaller C3-C6 range paraffins will not readily crack. To convert these compounds the paraffins are first converted to olefins over the dehydrogenation catalyst. To optimize the reactivity of the feedstock a balance has to be struck between cracking of olefins versus the generation of olefins from non-olefinic components, i.e. mainly paraffins. This balance will be a dependent on the feedstock and differ from the inlet to the outlet as the feed composition along the flow path will be different. The olefins will crack first and form light olefins. The composition of paraffins will change throughout the reactor as the paraffins that most readily dehydrogenate will do so after short residence time in the bed, relatively shortly after entering the reactor. The more stable paraffins will only be converted into olefins farther in the bed, or in some cases not at all. Therefore the optimal concentration profile for dehydrogenation catalyst and cracking catalyst will depend strongly on the composition of the feedstock.

In order to assess the catalyst system one may advantageously use normal decane as feedstock for a test reaction over the dehydrogenation catalyst, and 1-decene as feedstock for a test reaction over the cracking catalyst. By comparing the relative conversion rates in the claimed temperature range for the chosen catalyst system one may have a first insight on the relative activities of the dehydrogenation and cracking catalyst under investigation.

The process conditions may vary as a result of the combination of cracking catalyst and dehydrogenation catalyst. Suitably the temperature is between 300C and 750° C., more preferred between 400 and 650° C., most preferred between 450 and 600° C. The absolute pressure is suitably between 0.05 and 10 MPa and preferably between 0.1 and 0.5 MPa. It is preferred to reduce residence time, suppress coke make and reduce hydrocarbon partial pressure via dilution of steam. The reduction in hydrocarbon partial pressure boosts the dehydrogenation reaction, suppresses the reverse reaction, and suppresses the recombination of light olefins.

The Weight hourly space velocity, WHSV, as expressed in mass flow (per hour) divided by the mass of the catalyst is preferably higher than 20/hour and more preferably higher than and including 50/hour. Applicants found that by increasing the WHSV even more the olefin yield remains high while allowing the use of smaller reactor vessels. So for this reason a WHSV of above 100/hour is most preferred. This allows in use a lower feed rate than the design feed rate and still maintaining a high olefin yield. The feed is the hydrocarbon feed and any optional diluents, eg inert diluents. For example, a 30% dilution with nitrogen results in an increase of 30% in WHSV.

The process is carried out in one or more packed beds. By more than one bed is here meant any packed beds which are arranged in series with respect to each other. A similar second or even a third set of packed bed or beds may be arranged parallel to said first bed or beds. These second or third bed or beds may be used for performing the process according to the invention when the first bed or beds are regenerated to remove coke and optionally other contaminants. An example of such a regeneration process is when the reactors are operated as a simulated moving bed. It is also conceivable that not all packed beds in one set of beds in series are regenerated at a time. Instead a packed bed in a set of packed beds may have a longer run time as a result of the different catalyst composition with the packed bed and thus require less frequent regeneration than the remaining beds in the same in-series configuration.

If more than one packed bed in series is used to perform the process it may be advantageous to remove some of the low boiling reaction products including propylene from the reaction mixture in between the packed beds. This may be performed by means of a flash separation. The low boiling gasses thus obtained may be provided to a separation unit in which propylene is isolated from the reaction products of the most down-stream packed bed as will be described in more detail below. The higher boiling fraction as obtained in such a separation may be provided to the next bed or even internally recirculated to one or more of the up stream beds, optionally after reheating this fraction. The chosen recycle will depend on the olefin content in such a higher boiling fraction and the catalyst gradient in the packed beds. For example, when the content of the dehydrogenation catalyst relative to the total content of heterogeneous catalyst particles increases in the direction of the flow it may be advantageous to recycle to the more upstream beds when the olefin content is high. Such a direct recycle may also be performed with the higher boiling fraction as obtained when low boiling gasses are separated from the final effluent of the one or more packed beds.

The cracking catalyst and the dehydrogenation catalyst may also be present in one packed bed.

The propylene and optionaly the butylenes as formed in the process is/are suitably isolated from the effluent as discharged from the packed bed or beds from higher boiling compounds and wherein all or part of these higher boiling compounds are recycled to the packed bed or beds. In this separation propylene and optionally the butylenes will also be separated from other low and lower boiling compounds, such as for example ethane, ethylene, hydrogen and any water. Such a separation may include distillation and/or flash separation. It is found that almost no propane is formed in a great amount in the process. This is advantageous because this results in that no difficult propylene and propane separation is required to obtain a polymer grade propylene. In this separation ethylene as a valuable by-product may be isolated from the low boiling compounds. The C4 fraction including butane and butylene may be recovered as such or be recycled together with the higher boiling compounds to the packed bed or beds. Suitably the higher boiling compounds as obtained in this separation comprises for more than 90 wt % of hydrocarbons boiling above 75° C.

Any low boiling fractions separated from intermediate streams between the packed beds as described above may be fed to this separation. Such a fraction may contain some high boiling compounds because of the coarse separation and by feeding this fraction to this separation these high boiling compounds are recovered to be recycled to the packed bed or beds.

Preferably the hydrocarbon feedstock comprising olefin hydrocarbon as used in the process according to the invention has an aromatics content, i.e. a benzene, toluene and xylene content, of below 50 wt %, preferably below 20 wt % and even more preferably below 10 wt %. This aromatics content relates to the feedstock as being fed to the packed bed or beds and thus includes the so-called fresh feedstock optionally combined with the above referred to recycle of higher boiling compounds after these fractions have been subjected to the aromatic extraction step.

FIGURES

FIG. 1 shows a process scheme for a process to prepare propylene according to one embodiment of the present invention. Via stream 1 a hydrocarbon fraction boiling between 35 and 250 0C is mixed with a recycle stream 2 to obtain a combined stream. Combined stream is fed to an aromatics extraction unit 3 in which benzene, toluene and xylene are extracted from the mixture of hydrocarbons thereby obtaining a mixture of hydrocarbons poor in aromatics in stream 5 and a stream 4 comprising these aromatic compounds. The mixture of hydrocarbons poor in aromatics in stream 5 is mixed with a second recycle stream 6 to obtain a feedstock stream 8. The composition of recycle stream 2 and recycle stream 6 are the same in the process of this Figure. The mass flow of stream 2 and 6 may be different such that stream 2 is at least 5 wt % of the combined streams 2 and 6 (stream 7) and preferably between 10 and 30 wt % of the combined streams 2 and 6 (stream 7).

Feedstock stream 8 is raised in temperature in an indirect heat exchanger 9 against hot reactor effluent stream 10. The partly heated feedstock stream 8 is further increased in temperature in furnace 11 before being fed to the up-flow region 12 of the flow path as present in packed bed reactor 13. The flow path will run from the up-flow region 12 to the down-flow region 15 in packed bed 14. The furnace 11 may use for example fuel gas or fuel oil as fuel.

Part of the feedstock stream may be fed via stream 22 to an intermediate position in the flow path. This may be advantageous when the content of the dehydrogenation catalyst relative to the total content of heterogeneous catalyst particles increases in the direction of the flow. In such a configuration a feedstock stream 8 containing relatively low amounts of olefins may advantageously be recycled to an intermediate section of reactor 13 via stream 22.

Depending on the composition of the feedstock stream 8 a homogeneous mixture or a gradient of the cracking catalyst and dehydrogenation catalyst will be present in the packed bed 14 as described and explained above. Below the situation will be described for the embodiment wherein in the direction of the flow path the concentration of the dehydrogenation catalyst in the bed increases compared to the cracking catalyst. The up-flow region 12 of the catalyst bed will be primarily or exclusively cracking catalysts which will convert higher molecular weight olefins into propylene & butylene. The resulting olefin lean hydrocarbon mixture will then begin to contact more dehydrogenation catalyst in the reactor bed in the more down-flow regions 15. The paraffinic components of this mixture will be converted to high molecular weight olefins. These higher molecular weight olefins will subsequently quickly react with the cracking catalyst as present in the packed bed 14 obtaining the lower molecular weight ethylene, propylene and butylene products.

The rapid conversion of the high molecular weight olefins into low molecular weight olefins results in a significantly reduced coking tendency within the catalyst bed. This coking is a result of the interaction of the high molecular weight olefins with the dehydrogenation catalyst surface. The packed bed 14 may also comprise a solid oxygen source catalyst. The solid oxygen source catalyst will supply oxygen which in turn reacts with the formed hydrogen to water. Removal of the high molecular weight olefins and removal of hydrogen pushes the equilibrium dehydrogenation reaction in favour of more olefin production. The oxygen in the oxidation catalyst lattice will be recharged during the regeneration step.

The cracked effluent as being discharged from packed bed reactor 13 in stream 10 will comprise the desired propylene and ethylene, butylene and a higher boiling fraction comprising non-reacted feed stock and small amounts of aromatic by-products. The cracked effluent in stream 10 is reduced in temperature in indirect heat exchanger 9, air coolers 16 and chilled water trim coolers 17. Other methods of cooling are also possible. Propylene in stream 19 and optionally other valuable lower olefins may be separated from the cracked effluent in a single stage flash separation 18. Alternatively propylene and other olefins may be separated from the cracked effluent by means of one or more distillation columns or any other process sufficient to separate the light olefin product from the cracked effluent. From the remaining higher boiling fraction in stream 20 a part may be discharged as a purge via stream 21 to avoid a build-up of inert materials in the recycle stream. The remaining higher boiling fraction in stream 7 may be recycled to the aromatics extraction unit 3 and directly to the packed bed reactor 13 as described above.

Instead of recycling via stream 6 part of the stream 7 may be recycled via stream 23 to an intermediate position in the flow path in packed bed reactor 13. This may be advantageous when the content of the dehydrogenation catalyst relative to the total content of heterogeneous catalyst particles increases in the direction of the flow. In such a configuration a recycle stream containing relatively low amounts of olefins may advantageously be recycled to an intermediate section of reactor 13 via stream 23. The recycle stream 23 is preferably heated in a heater(not shown), like a heat exchanger and/or furnace. This configuration provides the operator of the process to optimise the recycle streams 2, 6 and 23 depending for example on the composition of stream 7.

A by-product of the dehydrogenation reaction, and to a lesser extent, the cracking reaction, is coke. One of the key discoveries of this present invention is the gradient of cracking catalysts mixed with the dehydrogenation catalysts which converts the coke precursors, i.e. the high molecular weight olefins, into ethylene, propylene & butylene before conversion to coke. Nevertheless, the packed beds of catalysts will require regeneration to burn the coke in the presence of oxygen into $CO_2$. A second reactor will be on stand-by for operation when the first reactor requires regeneration. The reactor just taken out of service will then be regenerated in preparation for its next cycle when the present reactor requires regeneration. This process will thereby continue without interruption.

The invention shall be illustrated by the following non-limiting examples.

EXAMPLE 1

A packed bed reactor was provided consisting of a mixture of a dehydrogenation catalyst and a cracking catalyst. The dehydrogenation catalyst was a typical platinum tin supported on alumina dehydrogenation catalyst. The cracking catalyst contained 50 wt % ZSM-5 in a silica-alumina-phosphate support. The content of dehydrogenation catalyst gradually increases from 0% at the start of the flow path for a hydrocarbon feed to 50 wt. % at the end of the flow path.

An FCC full range naphtha with 90% boiling point at 190° C. consisting of 34.9 wt % paraffins, 11.5 wt % naphthenes, 31.2 wt % olefins and 22.4 wt % aromatics was fed to the reactor at a 0.25 g/min in 50 ml/min nitrogen via the flow path at 500 and 550° C. The pressure in the reactor was 7 psig. The effluent was analysed and the results presented as (in weight percentages) are provided in Tables 1-2.

EXAMPLE 2

A packed bed reactor was provided having a single layer consisting of a 1:1 wt %/wt % mixture dehydrogenation catalyst and cracking catalyst. The dehydrogenation catalyst and cracking catalyst are the same as in Example 1. The total volume of the single catalyst layer was the same as the total volume of catalysts present in the reactor of Example 1. The FCC full range naphtha of Example 1 was fed to the reactor at a 0.25 g/min in 50 ml/min nitrogen via the flow path at 500 and 550° C. The pressure in the reactor was 7 psig. The effluent was analysed and the results are provided in Table 1.

TABLE 1

|  | 50:50 Blend Example 2 | | Gradient Example 1 | |
| --- | --- | --- | --- | --- |
|  | Temperature | | | |
|  | 500 | 550 | 500 | 550 |
| H2 + C1 + C2 | 0.9 | 2.0 | 0.6 | 1.7 |
| C3 | 2.0 | 2.5 | 2.3 | 2.9 |
| C3= | 5.8 | 7.4 | 7.8 | 9.6 |
| iC4 | 2.1 | 2.6 | 2.5 | 3.0 |
| nC4 | 1.2 | 1.5 | 1.4 | 1.7 |
| C4= | 5.1 | 6.6 | 7.0 | 8.6 |
| Gasoline | 82 | 76.1 | 78.1 | 72.1 |
| Coke | 0.9 | 1.3 | 0.3 | 0.4 |

EXAMPLE 3

A packed bed reactor was provided having a first layer of cracking catalyst and a second layer of dehydrogenation catalyst. The dehydrogenation catalyst and cracking catalyst are the same as in Example 1. The total volume of the two catalyst layers was the same as the total volume of catalysts present in the reactor of Example 1. A flow path for a hydrocarbon feed runs from the first layer to the second layer. The FCC full range naphtha of Example 1 was fed to the reactor at 0.25 g/min in 50 ml STP/min nitrogen via the flow path at 500 and 550° C. The pressure in the reactor was 7 psig. The effluent was analysed and the results are provided in Table 2.

TABLE 2

|  | Series Reactors Example 3 | | Gradient Example 1 | |
| --- | --- | --- | --- | --- |
|  | Temperature | | | |
|  | 500 | 550 | 500 | 550 |
| H2 + C1 + C2 | 1.3 | 3.9 | 0.6 | 1.7 |
| C3 | 2.0 | 2.7 | 2.3 | 2.9 |
| C3= | 5.5 | 6.5 | 7.8 | 9.6 |
| iC4 | 2.0 | 2.5 | 2.5 | 3.0 |
| nC4 | 1.2 | 1.4 | 1.4 | 1.7 |
| C4= | 4.9 | 5.7 | 7.0 | 8.6 |
| nC5 | 1.4 | 1.3 | 0.5 | 0.3 |
| iC5 | 9.9 | 9.8 | 2.4 | 2.1 |
| Gasoline | 81.5 | 74.5 | 77.9 | 71.5 |
| Coke | 1.6 | 2.8 | 0.5 | 0.9 |

The results in Table 2 show an improved yield for propylene in combination with a gasoline by-product which has substantially lower contents iso-pentane and pentane (part of the gasoline) which is beneficial for the Reid vapor pressure and the motor octane yield.

EXAMPLE 4

A mass balance is calculated for the process of FIG. 1. In this process FCC naphtha having a composition of 35.3 wt % olefins, 38.7 wt % paraffins, 8.5 wt % naphthenes and 17.5 wt % aromatics is provided to the process as stream 1. Reactor 13 has a packed bed as composed as in Example 1. In Table 6 the mass balance is provided for a situation wherein 20 wt % of stream 7 is recycled to aromatics extraction column 3 via 2 and 80wt % of stream 7 is recycled directly to reactor 13 via stream 6.

TABLE 6

|  | Stream (tons/hr) | | | | | |
| --- | --- | --- | --- | --- | --- | --- |
|  | 1 | 4 | 19 | 7 | 2 | 6 |
| FCC naphtha | 49 | | | | | |
| BTX | | 9 | | | | |
| Propylene | | | 25 | | | |
| Recycle | | | | 99 | 10 | 89 |

BTX = total of benzene, toluene and xylene

A sensitivity study is performed by varying the fraction of stream 7 which is send to aromatics extraction 3. In FIG. 2 the effect of varying this fraction on the total of feed in stream 7 is provided. This shows that when the fraction is above 10 wt % the flow rate in stream 7 is reduced significantly. The effect becomes less when this fraction is further increased. An optimum is between 10 and 30 wt %, wherein also the size of the aromatics extractor is taken into account.

The invention claimed is:

1. A process to prepare propylene from a mixture of hydrocarbons by performing the following steps:
    (a) extracting aromatics from the mixture of hydrocarbons thereby obtaining a resulting mixture of hydrocarbons poor in aromatics,
    (b) contacting the resulting mixture obtained in step (a) with a mixture of a heterogenous cracking catalyst and a heterogeneous dehydrogenation catalyst in a fixed bed thereby obtaining a cracked effluent,
    (c) separating propylene from the cracked effluent thereby also obtaining a higher boiling fraction, and
    (d) recycling a first recycle stream comprising between 10 and 30 wt % of the higher boiling fraction to step (a) and a second recycle stream comprising a portion of the higher boiling fraction to step (b), wherein the first recycle stream and the second recycle stream each comprise aromatic compounds originating from the higher boiling fraction.

2. The process according to claim 1, wherein the mixture of hydrocarbons comprises any one of:
    (a) between 1 and 70 wt % olefins having 4 or more carbon atoms;
    (b) between 1 and 20 wt % olefins having 4 or more carbon atoms; or
    (c) a mixture of paraffins, olefins, naphthenes, and aromatic compounds comprising more than 90 wt % hydrocarbons boiling between 35 and 250° C.

3. The process according to claim 2, wherein the mixture of hydrocarbons comprises a light straight run naphtha and/or a fraction isolated from an effluent of any one or more of the following processes: Fluid Catalytic Cracking, Catalytic Polymerization, Hydrotreating, Hydrocracking and Delayed Coking.

4. The process according to claim 3, wherein the mixture of hydrocarbons comprises:
    (a) a light straight run naphtha; or
    (b) a fraction isolated from the effluent of a Fluid Catalytic Cracking process.

5. The process according to claim 1, wherein step (b) is performed by contacting the resulting mixture obtained in step (a) with the heterogenous cracking catalyst to produce an intermediate mixture of hydrocarbons and contacting the intermediate mixture with the heterogenous dehydrogenation catalyst in the fixed bed to produce the cracked effluent from which propylene is separated in step (c).

6. The process according to claim 5, wherein the heterogeneous dehydrogenation catalyst comprises any one or more of:
   a. (i) a transition metal or a noble metal, (ii) one or more additive components, and (iii) a carrier;
   b. an oxydehydrogenation catalyst; and
   c. in that the one or more packed beds comprise a separate solid oxygen source catalyst particle.

7. The process according to claim 6, wherein the transition metal is Cr or the noble metal Pt.

8. The process according to claim 6, wherein the oxydehydrogenation catalyst, or the separate solid oxygen source catalyst particle, or both, comprises a reducible metal oxide of at least a transition metal.

9. The process according to claim 1, wherein step (b) is performed at a temperature between 300 and 750° C. and an absolute pressure between 0.1 and 10 MPa and a Weight hourly space velocity (WHSV) higher than and including 50/hour.

10. The process according to claim 9, wherein the temperature is between 450 and 600° C.,
   wherein the absolute pressure is between 0.1 and 0.5 MPa, and wherein the Weight hourly space velocity (WHSV) is higher than 100/hour.

11. The process according to claim 1, wherein in step (b) the resulting mixture obtained in step (a) is contacted with the mixture of the heterogenous cracking catalyst and the heterogenous dehydrogenation catalyst in the presence of dilution steam.

12. The process according to claim 1, wherein the heterogeneous cracking catalyst comprises an acidic material.

13. The process according to claim 12, wherein the acidic material is a molecular sieve, or an amorphous or semi-crystalline material chosen from the group of alumina, boehmite alumina, gamma alumina, theta alumina, silica alumina, silica-titania, silica-tungsten, silica phosphorous, and silica-alumina-phosphorous.

14. The process according to claim 13, wherein the molecular sieve is selected from the structure types consisting of: BEA, CHA, MOR, MFI, MEL, IMF and TUN.

15. The process according to claim 1, wherein the heterogeneous cracking catalyst:
   a. further comprises a carrier which does not have strong acidic sites, or
   b. does not comprise a molecular sieve and does comprise a material having strong acid sites.

16. The process according to claim 1, wherein the heterogeneous cracking catalyst and the heterogeneous dehydrogenation catalyst are separate catalyst particles.

17. The process according to claim 1, wherein the cracking catalyst and the dehydrogenation catalyst are present in one packed bed.

18. The process according to claim 1, wherein resulting the mixture obtained in step
   (a) has an aromatics content of less than 20 wt %.

* * * * *

UNITED STATES PATENT AND TRADEMARK OFFICE
CERTIFICATE OF CORRECTION

PATENT NO. : 10,479,740 B2
APPLICATION NO. : 15/737830
DATED : November 19, 2019
INVENTOR(S) : Hubertus Wilhelmus Albertus Dries Page 1 of 1

It is certified that error appears in the above-identified patent and that said Letters Patent is hereby corrected as shown below:

In the Claims

At Column 14, Claim 1, Line 36, "heterogenous" should be replaced with -- heterogeneous --.

At Column 15, Claim 5, Lines 3 and 5, "heterogenous" should be replaced with -- heterogeneous --.

At Column 16, Claim 11, Lines 3 and 4, "heterogenous" should be replaced with -- heterogeneous --.

At Column 16, Claim 18, Lines 29-30, "resulting the" should be replaced with -- the resulting --.

Signed and Sealed this
Twenty-eighth Day of January, 2020

Andrei Iancu
*Director of the United States Patent and Trademark Office*